United States Patent [19]

O'Leary

[11] Patent Number: 4,887,602
[45] Date of Patent: Dec. 19, 1989

[54] VENTILATED DIAPER OR INCONTINENT GARMENT

[75] Inventor: Audrey A. O'Leary, Belfair, Wash.

[73] Assignee: Weyerhaeuser Company, Tacoma, Wash.

[21] Appl. No.: 142,165

[22] Filed: Jan. 11, 1988

[51] Int. Cl.⁴ .............................................. A61F 13/16
[52] U.S. Cl. .............................. 604/305.1; 604/385.2; 604/389
[58] Field of Search ................... 604/385.1, 385.2, 393, 604/394, 397, 402

[56] References Cited

U.S. PATENT DOCUMENTS

| | | | |
|---|---|---|---|
| 4,036,233 | 7/1972 | Kozak | 604/385.2 |
| 4,381,781 | 5/1983 | Sciaraffa et al. | 604/372 |
| 4,425,128 | 1/1984 | Motomura | 604/381 |
| 4,591,523 | 5/1986 | Thompson | 604/358 |
| 4,596,568 | 6/1986 | Flug | 601/378 |
| 4,636,207 | 1/1987 | Buell | 604/370 |

*Primary Examiner*—Max Hindenburg
*Assistant Examiner*—K. M. Reichle

[57] ABSTRACT

The present invention is a diaper or incontinent garment of the usual construction having generally trapezoidal wing-like waist encircling portions at each end with a constricted crotch zone located between them. The waist encircling portions of at least one end, preferably at the rear, have discrete areas containing ventilating apertures. These areas are located between the absorbent pad and the lateral and transverse margins of the diaper. The use of this construction gives ventilation in the pad-free areas to reduce the incidence of diaper rash.

10 Claims, 1 Drawing Sheet

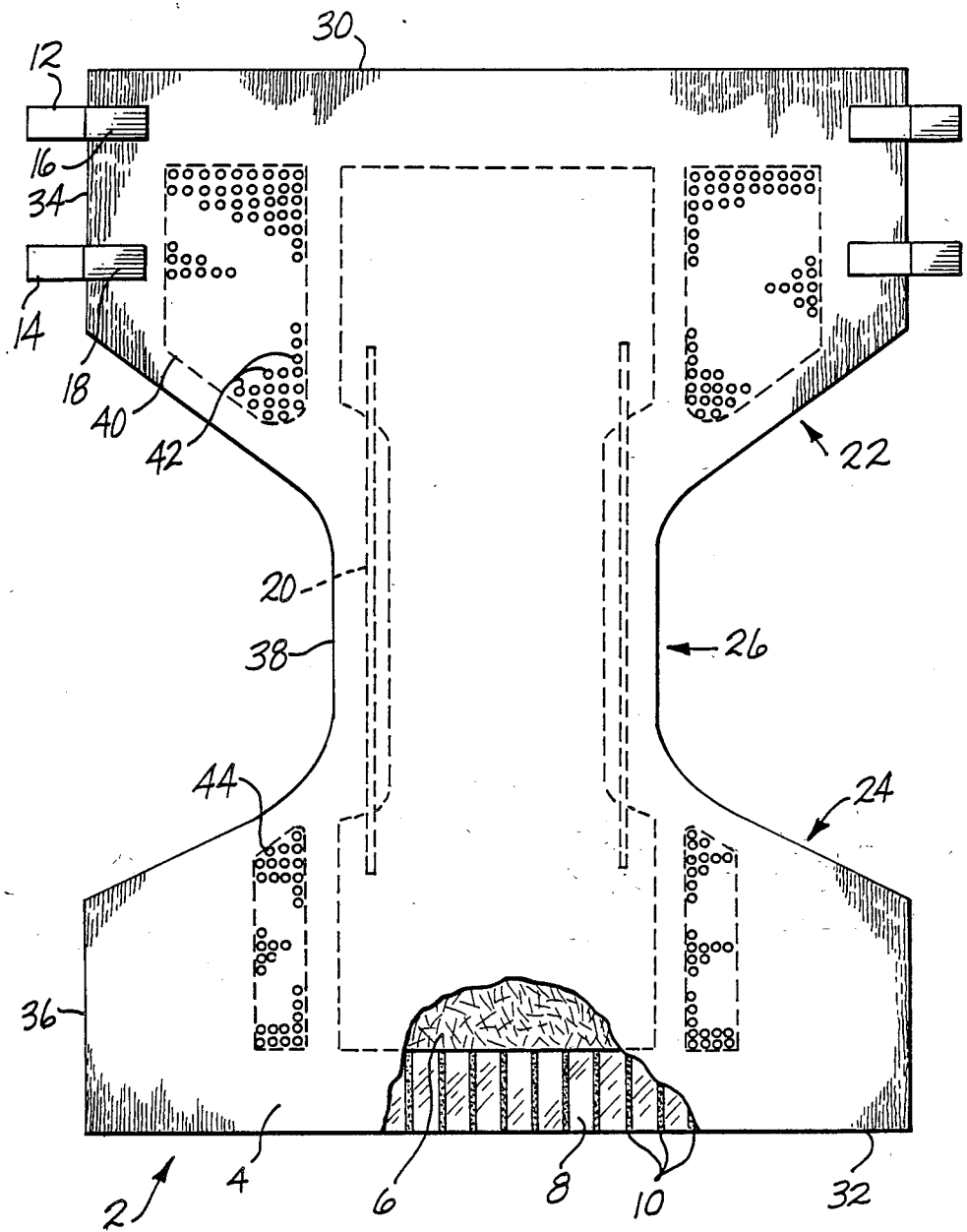

VENTILATED DIAPER OR INCONTINENT GARMENT

BACKGROUND OF THE INVENTION

The present invention is a diaper or incontinent pad in which certain nonabsorbing portions are apertured for ventilation and increased comfort to the wearer.

Considerable effort has been made in past years to increase the comfort of infant diapers or adult incontinent pads by making a wet product feel dryer to the wearer. This has principally been accomplished by the use of a relatively hydrophobic nonwoven fabric as the inner liner of the product. By maintaining the skin as dry as possible the growth of ammonia liberating bacteria on the skin can be reduced. In turn, this reduces irritation due to ammonia caused diaper rash. More recently, there has been a rapid appearance in the patent literature of diapers having moisture impermeable but vapor permeable backing sheets. While this construction does not reduce wetness, it does give ventilation which effects some reduction in bacterially generated ammonia. Patents to Motomura, U.S. Pat. No. 4,425,128 and Wilson et al, U.S. Pat. No. 4,701,170 may be taken as exemplary U.S. Pat. No. 4,636,207 to Buell shows a diaper with a ventilated leg cuff that may alternatively also have a breathable back sheet. Up to this time the so-called breathable back sheet material is relatively expensive and has not appeared on the market to any great extent. The ultimate success and effectiveness of a product using a breathable back sheet is to this point largely unknown.

The above references all pertain to diapers for infants. However, the problem of irritation can be much more serious where the wearer is an incontinent adult, especially a bedridden incontinent adult. Adult incontinent pads generally have a long and relatively narrow rectangular absorbent pad located along the longitudinal axis. A pad enclosing envelope of nonwoven material and moisture impervious backing film typically has relatively wide wing-like extensions at each end to serve as a waistband. These wings also form the sides of the garment. Irritation under these areas can be particularly severe due to the fact that there is a moisture and vapor impervious film held tightly against the skin.

As one answer to the above problem, some adult incontinent garments have been made without the waistband "wings". Instead, a relatively long attachment strap having adhesive ends has been substituted. This leaves the side of the wearer almost completely open. an example of a pad of this type is seen in U.S. Pat. No. 4,670,012 to Johnson. While pads of this type have found some commercial acceptance, they are not without their own problems. Leakage in particular is more difficult to control. While not related to the functional aspects of the incontinent pad itself, attendants in nursing homes have complained that the adhesive ends of the long attachment straps tend to get stuck to bedding before they can be positioned in place.

It would be desirable to have a diaper, and especially an adult incontinent pad, having the wing-type construction which was well ventilated but did not incur the expense of using presently available vapor permeable backing films. The present invention appears to admirably fill that need.

SUMMARY OF THE INVENTION

The present invention is a diaper or adult incontinent garment of the usual type comprising a moisture absorbing pad enclosed between a moisture permeable body contacting cover sheet and a moisture impermeable backing sheet. In a garment of this type the cover and backing sheets are generally coextensive and the pad is of smaller dimensions so that a pad free area or flange completely encircles the diaper. The diaper of the invention has pad-free generally trapezoidal wing-like waist encircling portions at each end with a centrally located constricted crotch zone so as to have an overall hourglass-shaped outline. The pad-free trapezoidal waist and side encircling portions of at least one end of the diaper have discrete areas with ventilating apertures. These areas are located between the absorbent pad and the longitudinal and transverse margins of the end portions. A single rather large aperture should be considered to be within the scope of the invention but it is preferred to have a plurality of smaller apertures within the defined areas. The apertures are generally in the range of about 3–25 mm in diameter. Preferably the apertures are about 5–10 mm in diameter.

In order to reduce leakage it is desirable that the areas containing the apertures be displaced at least about 25 mm from the pad. A similar margin should be maintained along any edge of the garment in order to avoid reduction of mechanical integrity.

The garment may have the ventilating apertures in the trapezoidal waist encircling portions at either or both ends of the garment. Most preferably the ventilated area at the rear waist encircling portions is larger than the ventilated area at the front waist encircling portions. It must be kept in mind that the waist encircling trapezoidal areas at the front are usually at least in part and often wholly covered by the real waist encircling portions when the diaper is in position on a wearer. For this reason any apertures placed in the front portion should be positioned so as to be generally outside the locations where they would be covered. It is further important that the apertures in the front portions be located where they are outside the region where an adhesive attachment tape might be placed. Otherwise, it is quite possible that the adhesive attachment device would be directly against the skin of the wearer if it was overlaying any of the apertures.

It is an object of the present invention to provide an improved diaper or incontinent garment having ventilated waist encircling portions.

It is another object to provide an improved diaper-type garment in which the waist portions can be ventilated simply and inexpensively using only conventional diaper making equipment.

These and many other objects will become readily apparent to those skilled in the art upon reading the following detailed description taken in the conjunction with the drawing.

BRIEF DESCRIPTION OF THE DRAWING

The single FIGURE is a top plan view, partially cut away, of an adult incontinent pad.

DETAILED DESCRIPTION OF THE PREFERRED EMBODIMENT

Referring now to the FIGURE, an incontinent pad, generally indicated at 2, comprises a moisture permeable nonwoven top sheet 4, an absorbent filler pad 6, and an impermeable back sheet 8. These are of conventional construction as is well known in the art. A plurality of parallel fine line hot melt adhesive strips 10 unites the components into a unitary assembly.

The diaper has a constricted crotch zone 26 with an extended generally trapezoidal rear waistband or wing portion 22 and a similar front waistband or wing portion 24. Attachment tapes 12, 14 are located along the longitudinal margins of the rear waistband portions. These are shown in extended position as they would be when the diaper was about to be placed on a wearer. Normally they would be pressed against release surfaces 16, 18 bonded to the nonwoven top sheet 4. One or more strips of elastic 20 will generally lie adjacent the longitudinal margins of the crotch area to reduce leakage from this zone of the garment.

The diaper has a rear transverse margin 30 and a front transverse margin 32. It also has a longitudinal margin 34 along the rear trapezoidal wing portion, a similar margin 36 along the front trapezoidal wing portion and a longitudinal margin 38 defining the crotch portion.

The rear wing portion 22 has a ventilated area 40 containing a plurality of apertures 42. Normally these are punched through both the top sheet 4 and a back sheet 8 although, if desired, it is only necessary that they be through the back sheet. Optionally, there may be a similar, although smaller, ventilated area 44 in the front trapezoidal wing portions. The apertures will generally be in the range of about 5-10 mm although, as noted earlier, they can be considerably smaller or larger.

In one version of the invention the entire area 40, and optionally area 44, may be cut out. This is generally not as desirable as the use of a plurality of apertures since fit may be adversely affected in some instances.

In the most preferred construction, the ventilated areas 40 and 42 will not extend very much beyond the transverse margins of absorbent pad 8. However, some ventilation of the areas immediately adjacent transverse margins 30 and 32 is permissible.

EXAMPLE

A standard medium size adult incontinent pad was made as follows. The cover sheet was thermally bonded polypropylene nonwoven material, Type APN-185, supplied by James River Corp., Washougal, Wash. The backing sheet was 0.033 mm (0.0013 in) polyethylene microtextured in a square pattern, available from Clopay Corporation, Cincinnati, Ohio. A bleached kraft pulp fluff pad was sandwiched between the cover and backing sheets and bonded to the latter using fine line hot melt adhesive strips placed on 19 mm centers. The fluff pad weighed about 92 grams and was generally rectangular, although constricted somewhat in the central portion, with dimensions of about 675 mm long, 230 mm wide at the ends and 160 mm wide in the center portion. There was a pad free waist portion about 75 mm wide at each end of the product. Trapezoidal wings (see the FIGURE at 22, 24) were located at each end of the product and were also pad free. The transverse dimension of the wing portion lying along rear end portion 30 was about 205 mm in width whereas the longitudinal side portion 34 was about 155 mm in length. The corresponding side portion lying adjacent to pad 6 was about 270 mm long.

A ventilated area 40, roughly in the form of an isosceles triangle having legs about 115 mm in length, was approximately centered in each rear wing portion. The base of the triangle lay along a line which was an extension of the line defining the end of pad 6.

The triangular ventilated area had 10 parallel rows of holes 6 mm in diameter cut through both the cover and backing sheets. There were 56 ventilation holes in each rear wing. These were located on a grid pattern on about 12 mm centers to create a ventilated area on each wing of about 16 cm$^2$.

Ventilation area could easily be doubled by increasing hole diameter to 8.5 mm while retaining the same center-to-center spacing. This would have little or no effect on the fit or structural integrity of the product.

Having thus described the best mode known to the inventor of practicing her invention, it will be apparent to those skilled in the art that many variations would be possible without departing from the spirit of the invention. Thus, the invention is to be considered as limited only by the following claims.

I claim:

1. An incontinent garment or diaper comprising a moisture permeable body contacting cover sheet, a moisture and vapor impermeable backing sheet, and a moisture absorbing pad disposed therebetween, the cover and backing sheets being generally coextensive and the pad being of smaller dimensions and located so that a pad free flange encircles the garment, said garment being of generally hour glass-shaped outline having front and rear end portions, adapted to encircle, respectively, the back and abdominal zones of the waist of a wearer, and a constricted central portion located therebetween adapted to fit the crotch zone of a wearer, said end portions having transverse and longitudinal margins, said opposite sides of each end portions defining generally trapezoidally shaped, pad-free wing-like portions comprising part of said flange, and ventilating apertures located only in discrete areas of at least the backing sheet of each of the wing-like portions at least at one end portions of the garment, said discrete areas being within boundaries of the absorbent pad and the transverse and longitudinal margins of the end portions of the garment.

2. The garment of claim 1 in which each discrete area contains a single large ventilating aperture.

3. The garment of claim 1 in which each discrete area contains a plurality of ventilating apertures.

4. The garment of claim 3 in which the apertures are at least about 3 mm in diameter.

5. The garment of claim 3 in which the apertures are in the range between about 3 and 25 mm in diameter.

6. The garment of claim 1 in which the discrete areas containing the ventilating apertures are displaced at least about 25 mm from the pad and from any marginal edge of the garment.

7. The garment of claim 6 in which the discrete areas do not extend beyond the ends of the pad in a longitudinal direction.

8. The garment of claim 1 in which the trapezoidal wing-like portions at both end portions have areas with ventilating apertures.

9. The garment of claim 8 in which the ventilated areas at the rear wing-like portions are larger than the ventilated areas at the front wing-like portions.

10. The garment of claim 8 which further has at least one pair of attachment tapes located in mirror image relationship on the rear wing-like portions and the ventilated areas of the front wing-like portions are positioned so as to be generally outside the locations where such tapes are adapted to be attached over the abdominal region of a wearer when the garment is in use.

* * * * *